United States Patent [19]

Ford

[11] Patent Number: 4,624,247
[45] Date of Patent: Nov. 25, 1986

[54] LEG BRACE FOR CONTROLLING SUBLUXATION

[75] Inventor: Edward I. Ford, Azle, Tex.
[73] Assignee: Medical Designs, Inc., Azle, Tex.
[21] Appl. No.: 812,008
[22] Filed: Dec. 23, 1985

Related U.S. Application Data

[63] Continuation-in-part of Ser. No. 693,143, Jan. 22, 1985, abandoned.

[51] Int. Cl.⁴ .............................................. A61F 3/00
[52] U.S. Cl. .................................. 128/80 C; 128/80 F
[58] Field of Search ................. 128/80 R, 80 C, 80 F, 128/80 H, 87 R, 88; 2/22, 24

[56] References Cited

U.S. PATENT DOCUMENTS

| | | | |
|---|---|---|---|
| 2,952,459 | 9/1960 | Moffitt | 128/80 H |
| 4,256,097 | 3/1981 | Willis | 128/80 C |
| 4,320,747 | 3/1982 | Daniell, Jr. | 128/80 C |
| 4,379,463 | 4/1983 | Meier et al. | 128/80 C |
| 4,428,369 | 1/1984 | Peckham et al. | 128/80 C |
| 4,487,200 | 12/1984 | Feanny et al. | 128/80 F |

FOREIGN PATENT DOCUMENTS 131798  8/1932  Austria .............................. 128/80 C

*Primary Examiner*—William R. Cline
*Attorney, Agent, or Firm*—James C. Fails; William T. Wofford; Arthur F. Zobal

[57] ABSTRACT

An improvement in a knee brace for alleviating problems with tibia rotation, subluxation and migration with respect to a femur of a wearer, including conventional first and second pairs of elongate braces having their respective hinges connected at their central ends, characterized by the improvement in the form of a plurality of 8 flexible, inelastic, non-metallic bands connected at the plurality of points of fixation anteriorly and posteriorly of the respective braces for tightening to fit any leg and lie close to the leg. In a preferred embodiment, the respective plurality of straps connected to their respective D-rings anteriorly and posteriorly of the braces include a de-rotation pad for being held tightly adjacent the tibia at the inside anterior of the tibia to prevent rotation of the tibia. In still more preferred embodiments, a cover of Ensolite foam is provided for the hinge and braces to allow the knee brace to be used in sports; and the hinge has diverging slots for facilitating access to the limiters of the degrees of flexion and extension. By this structure, one size can fit all, either right or left legs and the universal adjustability of all facets and elements make for a flexibility and freedom without loss of support (not heretofore available).

6 Claims, 5 Drawing Figures

U.S. Patent Nov. 25, 1986 Sheet 1 of 3 4,624,247
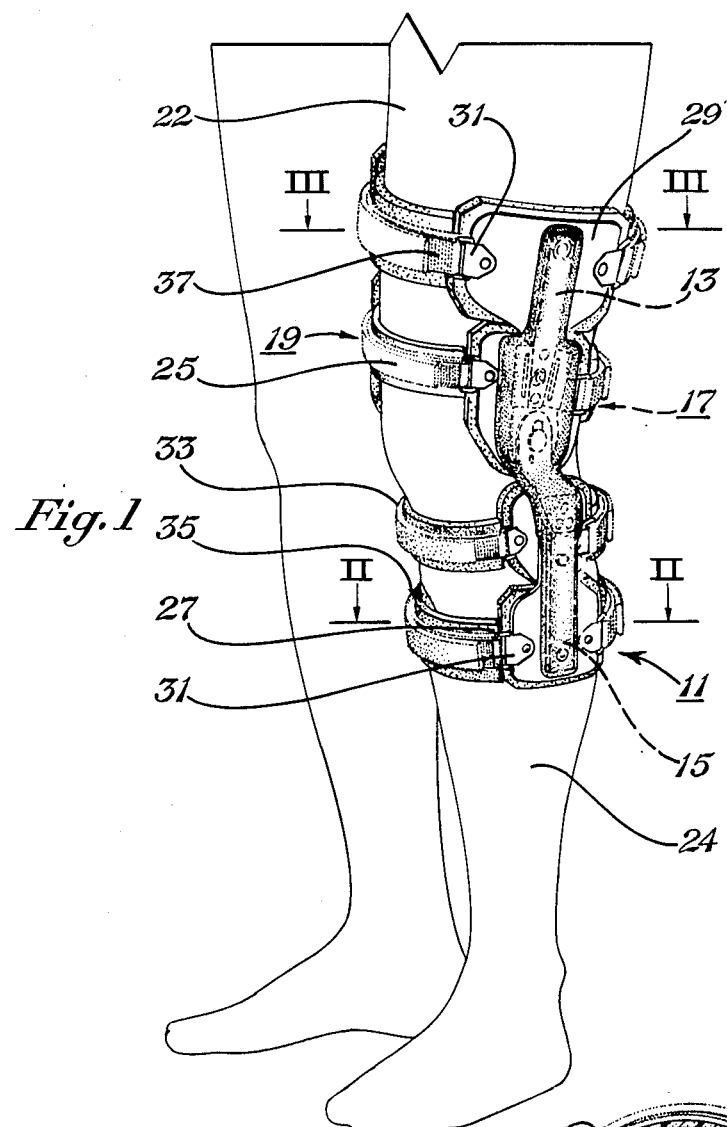
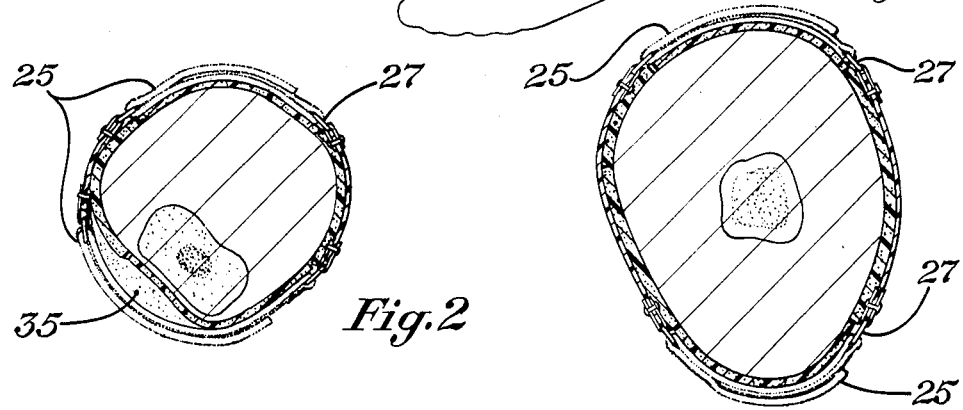

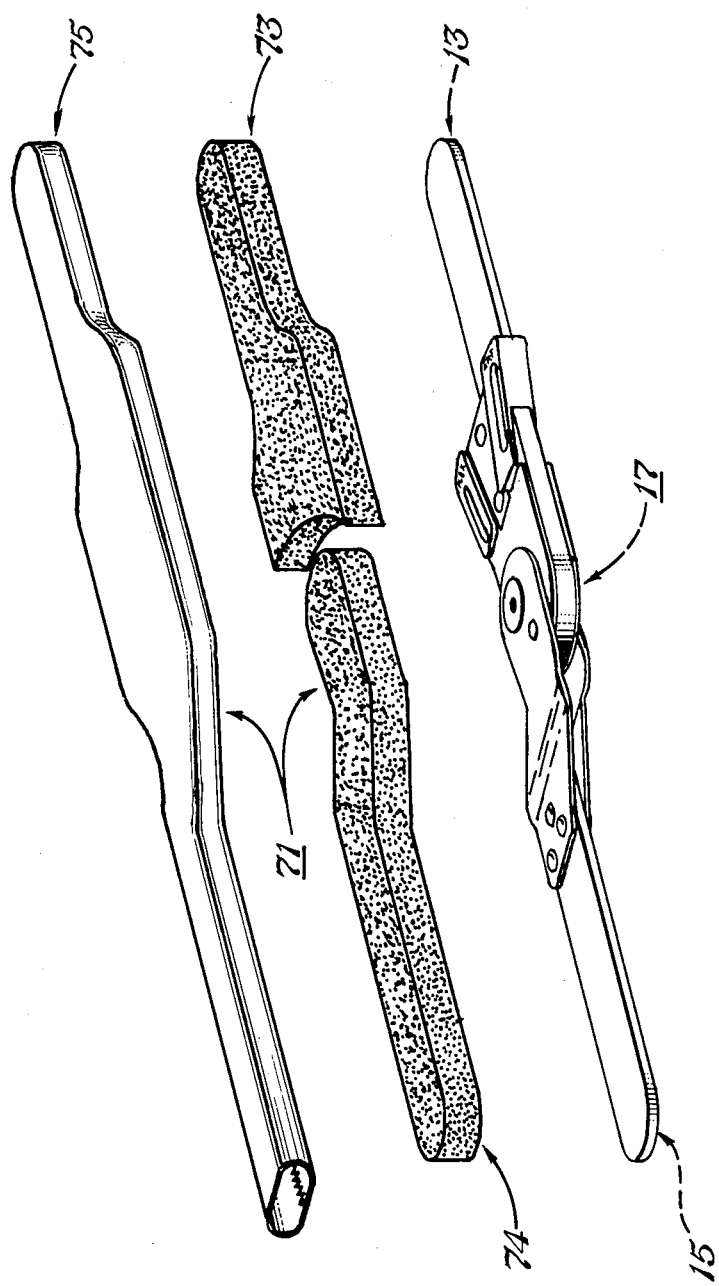

LEG BRACE FOR CONTROLLING SUBLUXATION

CROSS REFERENCE TO RELATED APPLICATION

This application is a continuation-in-part application of U.S. Ser. No. 693,143 field Jan. 22, 1985, now abandoned, same inventor and same title.

FIELD OF THE INVENTION

This invention relates to a knee brace. More particularly, it relates to a hinged leg brace for alleviating problems with rotation and subluxation of a tibia with respect to a femur in the leg of a wearer, even while engaged in strenuous activities.

DESCRIPTION OF THE PRIOR ART

A wide variety of approaches have been employed in the prior art for braces for legs and the like. Thus, for example, reference may be had to U.S. Pat. Nos. 618,097; 1,228,113; 2,144,641; 2,308,776; 3,528,412; 3,581,741; 3,669,105 for various types of knee braces for protection of knee joints and the like. None of these prior art braces have been totally satisfactory in preventing or alleviating problems with rotation of the tibia with respect to the femur as a primary problem; or subluxation of the tibia with respect to the femur. A germane invention was described and claimed in U.S. Pat. No. 4,407,276 entitled "BRACE FOR ARTICULATED LIMBS", Bledsoe, issued Oct. 4, 1983, assigned to the assignee of this invention and the contents of that patent are incorporated herein by reference for details that are omitted herefrom.

In addition, applications on improvements have been filed by other co-workers and been given Ser. Nos. 473,229, entitled "KNEE BRACE HINGE", filed Mar. 8, 1983 now U.S. Pat. No. 4,489,718 by Kelsey Martin and assigned to the assignee of this invention; Ser. No. 488,268 "BRACE FOR KNEE", filed Apr. 25, 1983 now U.S. Pat. No. 4,487,200 and Ser. No. 511,265, "DEROTATION LEG BRACE", filed July 6, 1983, now U.S. Pat. No. 4,503,846. All delineated improvements directed to the hinge are to structure employing metal cuffs anteriorly of the tibia and posterior of the femur. The files of these patent applications show a good review of prior art in the United States patents and in general. A portion of that material will be repeated herein to give the reader an understanding without requiring reference to another instrument.

Doctors and other technicians frequently impose restraints on a person's bones, joints and connective tissue to allow natural healing to be started or completed before restraints are released or broadened. Broadening allows additional movement and alleviates problems with atrophying of the muscles or the like. The new thinking is apparently to eliminate as much as possible of the bulky conventional cast and to wear temporary apparatus that can be removed to prevent problems with skin maceration, to accomodate changes as healing of the injury takes place and to allow better attention to personal hygiene and the like.

In those file histories, also, were discussed groupings of knee braces and the like ranging from the immobilizers which did not have a hinge and are not discussed herein; through braces that are relatively permanent for longer term wear such as those disclosed in U.S. Pat. No. 2,632,440; 2,943,622; 3,826,251; 3,827,431; and 3,844,279. These long term braces did not have the rotation and subluxation control and cuffs of the improved inventions. Typical of the apparatus that employs the hinge with knee braces are those shown in the following U.S. patents: U.S. Pat. No. 3,575,166 describes apparatus in which two rigid bodies, or covers, partially encircle a person's thigh and calf, respectively, encompassing about 270° of the wearer's leg member and employing a flexible elastomeric material to fill in the remaining 90° gap. A single hinge is rigidly connected on each side of the thigh and calf cuffs in order to provide some control with regard to a person's knee movements. U.S. Pat. No. 3,581,741 discloses similar "body" portions 18, 28 which are described as being a tough polymeric plastic material which may be internally reinforced with glass fibers and the like. U.S. Pat. No. 3,669,105 discloses a construction which has the advantage of being manufactured and worn by athletes having weakened knees. U.S. Pat. No. 3,785,372 describes a relatively complicated hinge apparatus. U.S. Pat. No. 3,786,804 describes apparatus having a single piece cylindrical sleeve of elastic material with loosely fitting pockets. U.S. Pat. No. 4,220,148 discloses a stabilizer but does not disclose the aspects of this invention. U.S. Pat. No. 4,233,967 discloses a plastic construction for attaching pairs of elongated braces but does not have the structure of this invention. U.S. Pat. No. 4,241,730 discloses a knee support which includes a pair of pivotally interconnected rigid braces but does not include the structure of this invention; U.S. Pat. No. 4,271,831 describes a knee brace having upper and lower sections that encase the proximal and distal members of the leg and have a hinge therebetween but do not have the structural features of this invention; U.S. Pat. No. 4,271,831 describes a knee brace having upper and lower sections that encase the proximal and distal members of the leg and have a hinge therebetween but do not have the structural features of this invention.

In the delineated prosecution histories there can be found references such as the following: U.S. Pat. No. 3,826,251 describes a hinge with a locking joint that locks under weight but is pivotal when the weight is released; U.S. Pat. No. 4,252,111 discloses a locking mechanism for locking a hinge through a movable pin that is inserted into mating apertures; U.S. Pat. No. 4,353,631 discloses an orthotic-prosthetic joint for supporting an infirm anatomical knee while permitting normal motion. The structure contains end portions that are secured to parallel connecting members for independent movement with concealed stops disposed intermediate to end portions and having a reinforced corrugation 20 on the upper assembly with a large calf cuff of custom molded plastic in the lower assembly. U.S. Pat. No. 4,361,142 discloses a knee orthosis and joint construction for protective treatment of ligaments during healing. There is a fairly complicated hinge structure with a single condyle pad and encircling straps.

Also, prosecution histories reveal the following U.S. Pat. Nos.: 4,271,831 shows a knee brace with encircling straps for tying rigid bars to the front of the tibia and include a drift control device. U.S. Pat. No. 3,581,741 describes a knee brace having an encircling upper rigid body portion and a lower rigid body portion with straps for controlling movement about the medial and lateral meniscus. U.S. Pat. No. 4,387,709 describes a knee brace having a substantially complete, openended tubular shell in an integrally formed piece of semirigid material shaped to fit a particular leg adapted to be slipped on and off, and having straps to hold it closed. U.S. Pat. No. 4,144,592 describes a knee guard for disposition along with the thigh of the user for protecting the knee with internal pads and having straps that hold a rigid front onto the wearer or the user as in a football uniform.

It has been found desirable to provide a knee brace that has the following features not heretofore provided by the prior art:

1. The knee brace should have 8 flexible non-metallic straps that lay closer to the leg than the prior art.
2. The straps should have 16 individual points of fixation, both front and back, of respective braces and hinge means to be individually adjusted so that one size can fit any leg; yet that can be tightened comfortably to control both subluxation and rotation.
3. The straps should be padded both anteriorly and posteriorly of the leg for comfort.
4. The brace should have dual condyle pads that are adapted to fit the supracondylar area closely to support the condyle (bone knuckle) on both the femur and the tibia.
5. These condyle pads should be fully adjustable to any length or circumferential placement. In this way the condyle pads allow free movement without bunching of the condyle pads or introducing discomfort; yet, continue to support the condyle on their respective elements.
6. The knee brace hinge needs, in addition to non-stretch, flexible straps to compensate for laxity in ligaments, a hinge that has diverging slots to facilitate access to adjusting the control elements that control the degress of freedom in flexion and extension.
7. It is desirable that the knee brace hinge have suitable covers such that it can be employed in sports or the like without endangering any other participants in the sport, as well as being safe for the wearer.

In the foregoing paragraph it can be seen that the prior art has not provided these desirable features.

SUMMARY OF THE INVENTION

Accordingly, it is an object of this invention to provide a knee brace that alleviates the deficiencies of the prior art, particularly with respect to the rotation and subluxation of the tibia with respect to the femur and that provides one or more of the features delineated hereinbefore as desirable and not heretofore provided by the prior art.

It is a specific object of this invention to provide a lightweight knee brace that can be readily removed or adjusted, and alleviates problems with swelling, muscle atrophy, and hygiene; as well as providing all of the features not heretofore provided by the prior art.

These and other objects will become apparent from the descriptive matter hereinafter, particularly when taken in conjunction with the appended drawings.

In accordance with this invention, there is provided a knee brace for alleviating problems with rotation and subluxation of the tibia with respect to the femur in the leg of a wearer, including:

a. a first and second pairs of elongate braces, with each of the braces being relatively stiff so as to resist both torsion and bending loads, the first pair of elongate braces being adapted to lie on opposite sides of and closely adjacent the wearer's thigh and the second pair of elongate braces being adapted to lie on opposite sides of and closely adjacent the wearer's calf;

b. a pair of respective hinge means connected respectively with the first and second pairs of braces at their respective central ends for allowing controlled flexion and extension of the wearer's leg;

c. means for adjustably placing and holding the respective pairs of elongate braces in the desired position on the respective opposite sides of the wearer's thigh and calf with the hinge means positioned directly adjacent the wearer's knee; and the improved construction for alleviating problems with rotation and subluxation of the tibia with respect to the femur. The improvement is characterized by:

d. a plurality of eight (8) flexible, inelastic, nonmetallic straps that are fully adjustable and adapted to fit any size leg;

e. a plurality of sixteen (16) attaching D-ring means for affixing respective straps, eight (8) D-ring means being connected at the anterior of the braces above and below the hinges and eight (8) of the D-ring means connected at the posterior of the braces above and below the hinges, the D-ring means defining respective individual points for affixing the plurality of eight (8) straps above and below the hinge means such that one size fits any leg to control subluxation and distal migration and compensates for laxity of ligaments in the leg; and f. a plurality of eight (8) pads disposed interiorly of and connected respectively with the straps for comfort when the straps are closed tighly about the wearer.

In preferred embodiments there are employed low density polyethylene plastic chafe tabs intermediate the D-ring means and the braces with riveted construction; with shaped foam pads; with the covered hinge option for use in playing sports; and dual condyle pads on each side, each condyle pad being contoured to fit closely the supracondylar region and support the condyle (bone knuckle) of the respective femur and tibia. Any other suitable plastic could be employed in the chafe tabs.

It is believed helpful to have a broad discussion of this invention before considering the detailed aspects. The knee brace attaches to the thigh proximally with both anterior and posterior inelastic straps that coact with the plastic connected to the braces to encompass the posterior, medial, lateral and anterior aspects of the thigh. A soft Ensolite (trademark of Uniroyal for vinyl sponge) liner is employed to facilitate pressure against the skin. Specifically, the straps are preferably elongate straps with Velcro attachments to be able to be affixed at any length. In this fashion the thigh is grasped firmly. Descending from the proximal thigh are the braces which run to the hinge and thence to the calf. The hinge facilitates adjustment through a particular construction and allows controlled flexion and extension of the knee joint as discussed in more detail hereinafter. The braces may be contoured to the shape of a leg either right or left such that one size fits all in a truly universal design. The braces are hinged with a hinge that has a cam design which allows the brace to flex and extend simulating the normal articulated cam effect of a normal knee joint. On the inner aspect of each hinge are a pair of respective contoured condyle pads on each side. The condyle pads are made of a soft Ensolite foam material contoured to fit the supracondylar region and to rest against the medial and lateral femoral and tibial condyle of the knee and hold the brace in place and the condyles at their respective desired positions. The straps run above the patella across the front of the knee and the lower straps run below the level of the patella at the level of the tibial tubercle of the insertion of the patella tendon. This lower strap has been moved inferiorly so that flexion and extension does not cause the strap to be a leverage to push the brace upward on the leg as the patella or kneecap travels over the front of the knee. The contoured condyle pads are fixed by a riveted type piece of polyethylene plastic attachement to the inner aspects of the hinges.

The plastic should be semi-rigid so as to provide support, yet conform to fit the individual. Specifically, the plastic should have a Shorr hardness in the range of 40-60.

The lowermost, or bottom, strap is attached to a wedge that is universally adjustable and can be attached to closely fitted flat surface medially on the subcutaneous border of the tibia so that it can gain purchase to the subcutaneous border. The outer edge of the wedge is rounded to rest against the strap and the inside shaped to engage the interior of the tibia to grasp the leg firmly by its anatomical configuration. Preferably, the wedge is removably attached, as by Velcro.

BRIEF DESCRIPTION OF THE DRAWINGS

FIG. 1 is an isometric view showing one embodiment of this invention.

FIG. 2 is a partial cross-sectional view taken along the line II—II of FIG. 1.

FIG. 3 is a partial cross-sectional view taken along the line III—III of FIG. 1.

FIG. 5 is an exploded view of the hinge and cover of FIG. 1.

DESCRIPTION OF PREFERRED EMBODIMENTS

Figure 4:
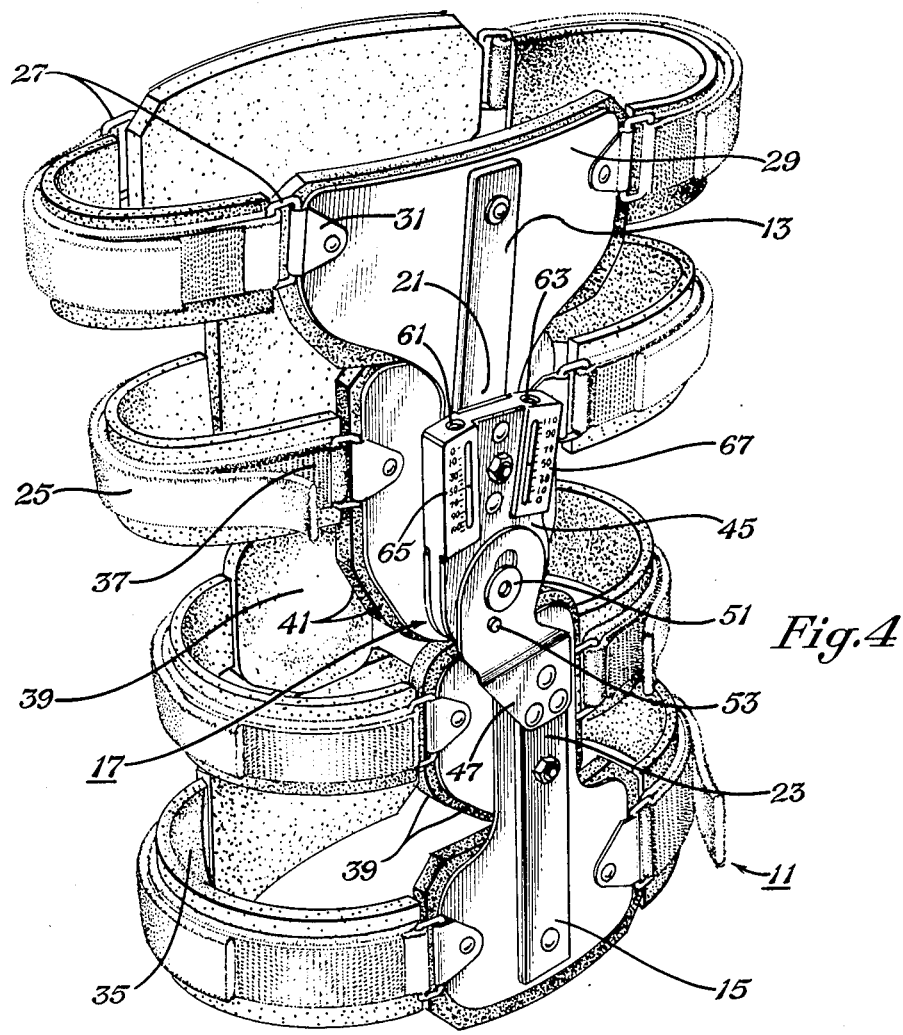
FIG. 4 is an isometric view of the knee brace of FIG. 1.

This invention will be described as employed in allowing the healing of a leg injury in preventing rotation and subluxation, as well as longitudinal dislocation of the tibia with respect to the femur of the leg; although it may be useful in other applications.

Referring initially to FIG. 1, the knee brace 11 is illustrated in position for controlling the degree of flexion, extension and lateral motion and longitudinal migration that is permitted by wearer's distal member with respect to its proximal member while controlling rotation and subluxation of the tibia with respect to the femur. The knee brace 11, FIGS. 1 and 4, includes first and second pairs of uprights or braces 13, 15, hinge means 17 and means 19 for adjustably placing and holding the respective pairs of elongated braces 13, 15 and hinge means 17 in a desired correct attained position on opposite sides of the thigh, knee and calf of the wearer.

Each of the braces is relatively stiff so as to resist both torsion and bending forces, or loads. A preferred structural material for the core of the brace is an elongate piece of aluminum having predetermined width and thickness; for example, about 2 centimeters wide and about 3 millimeters thick. The respective braces have their central ends, 21, 23, FIG. 4, connected with their respective hinge means 17. The braces are adapted to be positioned on opposite sides of the wearer's thigh and calf. As illustrated, the first pair of braces are adapted to be placed on respective sides of the wearer's thigh 22 closely adjacent the leg. The second pair of braces are adapted to be emplaced along respective sides of the wearer's calf 24 and closely adjacent the leg.

Any other structurally strong bracing material can be employed. The type bracing material employed in the prior art may be employed herein and the respective braces, whether or not they are affixed to plastic or other materials, such as Velcro, for being held in place, will depend on the type of means 19 for holding them in place and upon the hinge means 17.

The hinge means 17 may comprise any of the satisfactory hinge means of the prior art. Preferably, the hinge means 17 will be a complex hinge that is able to accomodate simulated motion of an actual knee requiring a compound center of rotation, such as described in a co-pending application entitled "KNEE BRACE HINGE", Ser. No. 473,229, inventor Kelsey (no middle initial) Martin, filed 3/8/83 and assigned to the assignee of this invention; and the descriptive matter of that patent application is incorporated herein by reference for details that are omitted herefrom. In that application, there was disclosed means for limiting the degrees of pivotal movement in extension and flexion of the calf with respect to the thigh, and hence of the tibia with respect to the femur. Specifically, the hinge means of that application had indices and an indicator that could be screwed to limit the range of motion that the wearer would have. Of course, other types of hinges have been known in the prior art and as long as they are satisfactory to the doctor employing the knee brace of this invention, they may be employed. As described in the aforementioned U.S. Pat. No. 4,407,276, "BRACE FOR ARTICULATED LIMBS", the type of hinge means is not critical to this invention. It should be compatible with the means 19 for holding the braces in place, however.

The means 19 for placing and holding the braces in a correct desired attained position comprise, in this invention, a plurality of eight inelastic, non-metallic straps that are padded on their interior for comfort and that can be tightened to the desired degree to prevent rotation and subluxation of the tibia with respect to the femur, as well as prevent and control distal migration and compensate for laxity of the ligaments in the leg.

In accordance with this invention, FIGS. 1-4, the plurality of straps 25 are connected, as by a way that includes D-ring means 27 at both the anterior and posterior of the respective braces. As illustrated, semi-rigid polyethylene plastic pieces 29 are connected with the respective braces 13 and 15, as by being riveted thereto, and are in turn riveted to the straps 31 on the D-ring means 27. Any suitable plastic having Shorr hardness of 40-60 could be employed. As illustrated, there are plurality of 8 anterior D-ring means and 8 posterior D-ring means to which respectively, 4 anterior straps and 4 posterior straps are connected in fully adjustable manner so as to be able to be tightened to any desired degreee of tension. Expressed otherwise, the D-ring means affixing the respective straps are located on the anterior of the braces above and below the hinges and on the posterior of the braces above and below the hinges. The connection of the D-ring means is indirectly through the rigid one or more pieces of plastic 29. A plurality of respective pads 33 are interposed interiorly of the respective straps 25 for comfort when the straps are tightened to the desired snuggness of fit.

Preferably, direct engagement of the respective tibia wedge and the condyle pads is achieved by using the straps 25 with their respective individual D-ring means 27 for attaching them and for tightening to the desired tightness front and back to complete the encirclement of the thigh or the calf of the wearer. Ordinarily these straps include Velcro tabs such that they can be affixed on one side and then pulled through to the desired adjustment and folded back to fasten to the Velcro tabs. The straps also hold the padded wedge 35, FIGS. 1 and 2, in place adjacent the interior front of the tibia to prevent rotation. The Velcro may be seen by the reference numeral 37, FIG. 1 onto which the respective straps ends are folded back for fastening. As is well recognized, the Velcro and related material comprise a series of J-shaped hooks that engage loops and hold a desired attained position or tautness.

The respective straps and their coacting and co-engaging D-ring means, together with their tabs, plastic, and metallic braces or hinges, enable complete encirclement of the leg of the wearer at either the thigh or the calf and have the advantages delineated hereinafter. The primary improvement of one aspect of this invention is the use of the flexible, inelastic straps that are fully adjustable and are adapted to fit any size leg with the attaching at the anterior and posterior with their respective sets of D-ring means for affixing the straps above and below the hinge means; in combination with the plurality of pads disposed interiorly of and connected with the straps and the pairs of braces so as to control subluxation, rotation and distal migration of the tibia. The pads 33, as well as the condyle pads 39, 41, are preferably formed of a resilient material. An excellent material has been found to be Ensolite, which forms a superior foam pad. As is recognized, Ensolite has a density in pounds per cubic foot (PCF) in the range of 3.5 to 8.5. Of course, other forms of resilient material such as foam rubber and the like could be employed if desired.

The hinge means 17 includes a single cam slot operator, a first member having a slot simulating the path of traversal in flexure of the wearer's knee and at least one second member having a cam means engaging the slot so as to traverse the slot in flexion or extension flexural motion. The first member and at least one second member co-engage each other and are adapted to move pivotally with respect to each other about a central shaft 31 engaging the respective aperture and slot, as described in the afore mentioned Ser. No. 473,229 in more nearly complete detail. As illustrated, and preferably, the hinge means 17 includes two second members 47 sandwiching therebetween a first member 45, FIG. 4 with a slot extending completely through the first member. In this way the cam comprises a pin shaft that slidably engages the slot yet locks the hinge together to restrict movement of the respective members with respect to each other and limit the flexion and extension of the wearer's lower leg, or distal member with respect to the femur. The positive lock for limiting the range of flexion comprises flexible plunger means; such as springs (not shown); that are movably disposed in the respective ends of the slot for restricting movement of the cam; and threaded nuts; such as Allen-head nuts; for positioning the limits. Specifically, the slots terminate in respective threaded bores 61, 63, FIG. 4, and, respective, threaded nuts (not shown) are rotatably screwed into the respective threaded bores for moving the flexible plungers, or springs. Each of the nuts has an associate indicator that is moved longitudinally of indices 65, 67. As indicated, degrees are shown ranging, inversely from 0° to 110° of motion. Preferably the respective indicators may be of anodized aluminum; such as, red anodized aluminum or the like. If desired, they can be rotatably affixed to the respective nuts or plungers. Ordinarily, such affixing is unnecessary, since the plungers tend to follow and can be made to follow the nuts by flexure of the hinge means 17. The flexure causes the cam 51 to move the respective springs to maintain the indicators adjacent the respective nuts with which they are associated. This reduces the expense of a much more elaborate and respective interconnection therebetween.

The respective members of the hinge and nuts may be formed of any material. As illustrated, they are formed of aluminum to facilitate machining and the like. Of course, easily cleanable and relatively noncorrodible metal; such as, stainless steel; can be employed. In fact, mild steel or other materials can be employed, although special care must be taken to prevent corrosion or the like which can worsen the hygiene problems with such materials. If desired, on the other hand, plastic; such as, Delrin, Nylon or other machinable plastic can be employed.

In this embodiment, the bores 61, 63 are diverging at an angle in the range of 10° to 45°, preferably, 10° to 30° to facilitate access for tightening and loosening the respective nuts and indicators; yet, not so great an angle as to provide a wide hinge that would encumber operation. The angle is the angle between the central longitudinal axis of the bores and the central longitudinal axis of the brace 13 nearest thereto.

A cover 71, FIG. 5, comprises two pieces of ½ inch (") thick plastic foam 73, 74, preferably Ensolite, adhesively affixed, respectively, to braces and hinges and totally covered by a sewn together elastic sleeve 75, such as Neoprene or the like.

In operation, the knee brace is emplaced with the hinge adjacent the knee and the straps are tightened to the desired degree of tension about the calf and thigh of the wearer's leg. As indicated hereinbefore, the advantage of this invention is that the straps can be individually tightened to obtain the desired degree of tension and frictional engagement to prevent rotation, by way of holding the wedge 35 adjacent the anterior interior of the tibia, regardless of the size of the wearer's leg. The eight points of affixation, front and rear, with independently adjustable straps front and back control subluxation and compensate for laxity of the ligaments.

The hinges are emplaced with the internal two condyle pads on each side snugly engaging and supporting the condyles (bone knuckles) of the respective tibia and femur. The diverging slots on the hinge allow access to facilitate adjustment. A resilient cover of Ensolite foam or the like can be emplaced over the hinge if the knee brace is to be employed in sports or the like. Suitable covers can eliminate the requirement and expense of additional padding, tape and the like to satisfy regulations of sports authorities.

Thereafter, the adjustably placed wedge and attached pads are adjusted as necessary to maintain the desired degree of control, regardless of change of circumstance, as by slimming or fattening of the leg or the like. Moreover, the ease with which the brace can be changed increases personal hygiene of the wearer.

One of the advantages of this invention is that one size fits all. This is particularly useful from a warehousing and buying point of view. It also eliminates the necessity for custom fitting, molding and the like.

Another advantage of this invention is the exceptionally flexibility. For example, one doctor may order a brace for anterior subluxation control and medial ligament instability. In such a case a wedge is employed and is universally adjustable. Another doctor may only want to block extension or flexion to some maximum, such as 30°. In such case the wedge could be omitted.

From the foregoing it can be seen that all of the objects delineated hereinbefore have been effected.

Although this invention has been described with a certain degree of particularity, it is understood that the present disclosure is made only by way of example and that numerous changes in the details of construction and the combination and arrangement of parts may be resorted to without departing from the spirit and the scope of the invention, reference being had for the latter purpose to the appended claims.

What is claimed is:

1. In a knee brace for alleviating problems with tibia rotation, subluxation and migration with respect to a femur of the wearer, characterized by:
    a. first and second pairs of elongate braces with each of said braces being rotationally stiff so as to resist both torsion and bending forces; said first pair of braces being adapted to lie on opposite sides of the wearer's thigh and said second pair of braces being adapted to lie on opposite sides of the wearer's calf;
    b. a pair of respective hinge means connected respectively with the first and second pairs of braces at their respective central ends for allowing and controlling flexion and extension of the wearer's leg, and
    c. means for adjustably placing and holding respective pairs of elongate braces at desired attained positions on respective opposite sides of the wearer's thigh and calf with said hinge means positioned correctly adjacent the wearer's knee;
the improvement comprising:
    d. a plurality of eight flexible, inelastic, non-metallic straps that are fully adjustable and adapted to fit any size leg;
    e. a plurality of 16 attaching D-ring means for affixing respective straps, 8 said D-ring means being connected at the anterior of said braces above and below said hinges and a plurality of 8 said D-ring means being connected at the posterior above and below said hinges; said D-ring means being connected with said braces and defining respective individual points for affixing said plurality of the 8 straps above and below said hinge means such that one size fits any leg, controls subluxation and distal migration and compensates for laxity of ligaments in the leg; and
    f. a plurality of two contoured condyle pads on each side interiorly of each respective said hinge means, each pair of said two condyle pads allowing each segment of the leg to flex independently of the other without bunching either said condyle pad with respect to said condyle of either the tibia or the femur; said condyle pads being shaped, respectively, to fit the supracondylar regions of the tibia and femur, respectively, such that they support the condyle regardless of flexion or extension of the tibia with respect to the femur; said pads being disposed interiorly of and respectively connected with said straps and said pairs of braces for comfort of the wearer.

2. The knee brace of claim 1 wherein an adjustably placed wedge is attached to the bottom interior strap by Velcro and is movable circumferentially to a desired position for comfort and to control rotation of said tibia when said bottom interior is tightened in conjunction with said bottom posterior strap.

3. The knee brace of claim 1 wherein said condyle pads are two respective interior contoured plastic foam pads affixed to semi-rigid plastic interiorly of two longitudinally exterior pads affixed to the same type of semi-rigid plastic, the semi-rigid plastic being connected with said braces and said hinge means on each side of the brace so as to be held in place by said fully adjustable straps to fit any wearer's leg.

4. The knee brace of claim 3 wherein semi-rigid plastic is connected longitudinally of said braces with a second sheet of properly shaped plastic of same material connected interiorly of said first sheet of plastic and said braces and said hinge; each set of anterior straps has 8 D-ring means at the anterior and each set of posterior straps has 8 D-ring means at the posterior of said plastic for affixing of said flexible inelastic straps with the desired degree of tension and wherein there are 8 points of fixation with 16 respective Dring means for affixing said posterior and anterior inelastic straps; and wherein each strap has a plastic foam pad interiorly thereof for the comfort of the wearer.

5. The knee brace hinge of claim 1 wherein respective plastic foam covers $\frac{1}{2}$ inch ('') minimum thickness are provided for the right and left sides of the respective hinge means and respective braces such that said knee brace can be worn in sports activities without injury to other players.

6. The knee brace of claim 1 wherein each said hinge means has a single engaged cam and slot for simulating flexural motion of the wearer's knee and has a positive lock in the form of respective flexible plunger means that are movably disposed in respective ends of respective longitudinal slots and terminate in respective threaded bores with respective threaded nuts that are rotatably screwable into said respective threaded bores for moving said flexible plungers for restraining the movement of said cam, said bores diverging outwardly at an angle to facilitate access to the respective threadced nuts; said threaded nuts having associated indices and indicators for indicating the degrees of flexural motion permitted by said nuts and plungers.

* * * * *